United States Patent
Hornung et al.

(10) Patent No.: US 10,022,481 B2
(45) Date of Patent: Jul. 17, 2018

(54) CAPILLARY DIALYZERS

(71) Applicant: GAMBRO LUNDIA AB, Lund (SE)

(72) Inventors: Markus Hornung, Nehren (DE); Arnd Wochner, Dotternhausen (DE); Reinhold Buck, Alleshausen (DE); Helmut Hildwein, Voehringen (DE); Nikolaus Kanarjow, Hirrlingen (DE)

(73) Assignee: GAMBRO LUNDIA AB, Lund (SE)

( * ) Notice: Subject to any disclaimer, the term of this patent is extended or adjusted under 35 U.S.C. 154(b) by 223 days.

(21) Appl. No.: 14/893,688

(22) PCT Filed: Jun. 19, 2014

(86) PCT No.: PCT/EP2014/062922
§ 371 (c)(1),
(2) Date: Nov. 24, 2015

(87) PCT Pub. No.: WO2014/202710
PCT Pub. Date: Dec. 24, 2014

(65) Prior Publication Data
US 2016/0129172 A1    May 12, 2016

(30) Foreign Application Priority Data
Jun. 20, 2013 (EP) .................... 13172984

(51) Int. Cl.
| | | |
|---|---|---|
| *A61M 1/16* | (2006.01) | |
| *B01D 71/68* | (2006.01) | |
| *B01D 71/56* | (2006.01) | |
| *B01D 71/42* | (2006.01) | |
| *B01D 69/08* | (2006.01) | |
| *B01D 63/02* | (2006.01) | |

(52) U.S. Cl.
CPC ............ *A61M 1/1621* (2014.02); *A61M 1/16* (2013.01); *B01D 63/02* (2013.01); *B01D 69/081* (2013.01); *B01D 69/084* (2013.01); *B01D 71/42* (2013.01); *B01D 71/56* (2013.01); *B01D 71/68* (2013.01)

(58) Field of Classification Search
CPC ....... A61M 1/16; A61M 1/1621; B01D 63/02; B01D 69/081; B01D 69/084; B01D 71/42; B01D 71/56; B01D 71/68
See application file for complete search history.

(56) References Cited

U.S. PATENT DOCUMENTS

| | | |
|---|---|---|
| 3,616,928 A | 11/1971 | Rosenblatt |
| 8,202,428 B2 | 6/2012 | Heilmann |

FOREIGN PATENT DOCUMENTS

| | | |
|---|---|---|
| DE | 2851687 | 5/1979 |
| EP | 0305687 | 3/1989 |
| EP | 0844015 | 5/1998 |
| EP | 1257333 | 5/2006 |
| EP | 1714692 | 10/2006 |
| GB | 2009034 | 6/1979 |
| JP | S6422308 | 1/1989 |
| JP | H02258035 | 10/1990 |
| WO | WO2001/060477 | 8/2001 |

OTHER PUBLICATIONS

PCT International Search Report for PCT/EP2014/062922, completed Jul. 25, 2014.
Boschetti-de-Fierro, Adriana, et al., "Extended characterization of a new class of membranes for blood purification: The high cut-off membranes," Int J Artif Organs 2013; 36 (7): 455-463.

*Primary Examiner* — John Kim
(74) *Attorney, Agent, or Firm* — Barnes & Thornburg LLP

(57) ABSTRACT

The present disclosure relates to capillary dialyzers for blood purification comprising from 85-95% crimped fibers and from 5-15% non-crimped fibers.

14 Claims, No Drawings

CAPILLARY DIALYZERS

CROSS-REFERENCE TO RELATED APPLICATIONS

This application is the U.S. national phase of PCT/EP2014/062922, filed on Jun. 19, 2014. PCT/EP2014/062922 claims priority to European Patent Application 13172984.0, filed on Jun. 20, 2013. The disclosures of both European Patent Application 13172984.0 and PCT/EP2014/062922 are hereby incorporated herein by reference in their entireties.

TECHNICAL FIELD

The present invention relates to capillary dialyzers for blood purification.

BACKGROUND OF THE INVENTION

Capillary dialyzers are widely used for blood purification in patients suffering from renal insufficiency, i.e., for treatment of the patients by hemodialysis, hemodiafiltration or hemofiltration.

The devices generally consist of a casing comprising a tubular section with end caps capping the mouths of the tubular section. A bundle of hollow fiber membranes is arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2.

One important factor influencing performance of the device is the structure of the bundle of hollow fiber membranes. Several proposals for improving mass transfer between the flow spaces within the device by optimizing the structure of the bundle of hollow fiber membranes have been made:

DE 28 51 687 C2 discloses hollow, semi-permeable fibers having crimps with an average crimp period of less than 5 cm and a crimp amplitude of 15-250 µm. According to the reference, the relatively low amplitude crimps enable good fluid dispersion through a bundle comprising substantially parallel-oriented hollow fibers.

U.S. Pat. No. 3,616,928 A discloses a filter device comprising a plurality of hollow fibers aligned substantially parallel to one another in which each hollow fiber is crimped along its longitudinal axis such that it comprises a plurality of irregular bends.

JP 02/258035 A discloses a filter device comprising a bundle of hollow fibers having an outer diameter R of 200 to 500 µm; and 1 to 3.5 crimps per cm having a crimp amplitude L of $0.65*R \leq L \leq R+50$ µm.

EP 1 257 333 A1 discloses a filter device, preferably for hemodialysis, that consists of a cylindrical filter housing and a bundle of curled hollow fibers arranged in the filter housing. Each curled hollow fiber is provided with a sinusoidal texture and a wavelength defined by means of certain limits. The packing density of the fibers within the housing is in the range of from 60.5 to 70%, relative to the usable cross-section area of the housing which is calculated by multiplying the cross-section area by 0.907.

There is a continuing desire to further improve such capillary dialyzers, e.g., in terms of performance, efficiency, reliability, safety, handling, and other properties.

SUMMARY OF THE INVENTION

It has now been found that the performance of capillary dialyzers can be further improved by incorporation of fiber bundles comprising a specific proportion of crimped and non-crimped fibers.

DETAILED DESCRIPTION

The capillary dialyzers of the present invention comprise a housing and a bundle of semi-permeable hollow fiber membranes disposed therein, characterized in that the bundle of hollow fiber membranes comprises from 85 to 95% crimped fibers and from 5 to 15% non-crimped fibers, relative to the total number of fibers in the bundle.

The housing defines a longitudinally extending internal chamber including a first end and a second end. The internal chamber generally has a cylindrical shape. The bundle of semi-permeable hollow fiber membranes disposed within the internal chamber extends longitudinally from the first end of the housing to the second end of the housing, and the first end and the second end of the hollow fiber membranes correspond to the first end and the second end of the internal chamber.

End wall means support the first and second ends of the hollow fiber membranes within the internal chamber and separate the first and second ends of the hollow fiber membranes from the outer surface of the hollow fiber membranes between the first and second ends thereof. Thus a seal is provided between the first flow space formed by the fiber cavities and a second flow space surrounding the membranes on the outside.

Commonly, a first end cap covers the first end of the housing and a second end cap covers the second end of the housing, closing the ends of the housing in a fluid-tight manner. Each end cap features a port for the introduction of fluid into the first flow space of the dialyzer, or the evacuation of fluid from the first flow space of the dialyzer, respectively.

An inlet for the introduction of a fluid into the second flow space of the internal chamber and an outlet for the evacuation of a fluid from the second flow space of the internal chamber are provided at a location between the first and the second end of the housing.

Devices featuring this type of design are also disclosed in EP 0 844 015 A2, EP 0 305 687 A1, and WO 01/60477 A2.

According to the present invention, the bundle of semi-permeable hollow fiber membranes comprises from 85 to 95% crimped fibers and from 5 to 15% non-crimped fibers, relative to the total number of fibers in the bundle, for instance, from 86 to 94% crimped fibers and from 6 to 14% non-crimped fibers. In one embodiment, the proportion of crimped fibers is from 88 to 92%. The fibers have a sinusoidal texture with a wavelength in the range of from 6 to 9 mm, for instance, 7 to 8 mm; and an amplitude in the range of from 0.1 to 0.5 mm; for instance 0.2 to 0.4 mm.

The packing density of the hollow fiber membranes in the capillary dialyzers of the present invention is from 55 to 65%, i.e., the sum of the cross-sectional area of all hollow fiber membranes present in the dialyzer amounts to 55 to 65% of the cross-sectional area of the part of the dialyzer housing comprising the bundle of semi-permeable hollow fiber membranes. If n hollow fiber membranes are present in the bundle of semi-permeable hollow fiber membranes, $D_F$ is the outer diameter of a single hollow fiber membrane, and $D_H$ is the inner diameter of the part of the dialyzer housing comprising the bundle, the packing density can be calculated according to $n*(D_F/D_H)^2$.

Incorporation of 5 to 15% non-crimped fibers into a bundle of crimped semi-permeable hollow fiber membranes further improves the performance of the capillary dialyzer. For instance, at unchanged packing density of the fibers within the dialyzer, the clearance of molecules like urea, vitamin B12, or cytochrome C from a fluid passing through the fiber lumen is increased. It is believed that this effect is due to improved flow of dialysis liquid in the second flow space of the dialyzer and around the individual fibers in the bundle.

Another advantage of the incorporation of 5 to 15% non-crimped fibers into a bundle of crimped semi-permeable hollow fiber membranes is that packing densities can be achieved which are higher than those in bundles exclusively containing crimped fibers. As a consequence, a larger effective membrane area can be fitted into a given volume of the internal chamber of the capillary dialyzer. Alternatively, a given effective membrane area can be fitted into a smaller volume, which allows for further miniaturization of the capillary dialyzer.

Another alternative offered by the incorporation of 5 to 15% non-crimped fibers into a bundle of crimped semi-permeable hollow fiber membranes is that the crimp amplitude of the crimped fibers within the bundle can be increased at constant packing density and constant volume of the internal chamber, while the resilience of the bundle is kept at a value which does not require excessive force for the transfer of the bundle to the housing. This helps to avoid increased scrap rates in dialyzer production.

When less than about 5% of non-crimped fibers are present in the bundle of semi-permeable hollow fiber membranes, no substantial difference in dialyzer performance is observed in comparison to a dialyzer comprising crimped fibers only. On the other hand, when more than about 15% of non-crimped fibers are present in the bundle, a decrease of dialyzer performance is noted. A potential explanation for this effect could be that, with increasing proportion of non-crimped fibers within the bundle, non-crimped fibers may contact and adhere to each other, thus reducing membrane surface area available for mass transfer through the hollow fiber walls.

In one embodiment of the invention, the semi-permeable hollow fiber membranes comprise 80-99 wt % of polysulfone or polyethersulfone; and 1-20 wt % of polyvinylpyrrolidone (PVP).

Examples of suitable polysulfones are polymers having the general formula [Ph-C(CH$_3$)$_2$-Ph-O-Ph-SO$_2$-Ph-O—]$_n$, a weight average molecular weight of about 55,000 to 70,000 Da, a number average molecular weight of about 14,000 to 17,000 Da, and a $M_w/M_n$ of about 3.8 to 4.2.

An example of a suitable polyethersulfone is a polymer having the general formula [O-Ph-SO$_2$-Ph-]$_n$, a weight average molecular weight of about 60,000 to 65,000 Da, preferably 63,000 to 65,000 Da, and a $M_w/M_n$ of about 1.5 to 1.8.

In one embodiment of the invention, the PVP comprised in the semi-permeable hollow fiber membrane consists of a high (≥100 kDa) and a low (<100 kDa) molecular weight component and comprises 10-45 wt %, based on the total weight of PVP in the membrane, of a high molecular weight component, and 55-90 wt %, based on the total weight of PVP in the membrane, of a low molecular weight component.

In other embodiments of the invention, the semi-permeable hollow fiber membranes comprise a polyamide; a copolymer of acrylonitrile and sodium methallylsulfonate; or a polyacrylonitrile, respectively.

The hollow fiber membranes have an outer diameter of from 150 to 320 μm, for instance, 240 to 315 μm. The fiber bundle in the dialyzer has a diameter of from 20 to 50 mm, for instance, 30 to 40 mm. The effective fiber length within the bundle, i.e., the distance between the end wall means supporting the first and second ends of the hollow fiber membranes within the internal chamber, is in the range of from 120 to 280 mm, for instance, 210 to 270 mm.

In one embodiment, the wall of the semi-permeable hollow fiber membrane is asymmetric and has a sponge structure.

In another embodiment, the wall of the semi-permeable hollow fiber membrane is asymmetric and has a particular four-layer structure. The wall strength of the semi-permeable hollow fiber membrane of this embodiment is in the range of 25 to 50 μm.

The inner layer of the four-layer structure, i.e. the blood contacting layer and the inner surface of the hollow fiber membrane, is a separation layer in the form of a dense thin layer having, in one embodiment, a thickness of less than 1 μm and a pore size in the nano-scale range. To achieve high selectivity, the pore channels with the responsible pore diameters are short, i.e. below 0.1 μm. The pore channel diameter has a low variation in size.

The second layer of the hollow fiber membrane has a sponge structure and, in one embodiment of the present invention, a thickness of about 1 to 15 μm, and serves as a support for the first layer.

The third layer has a finger structure. It provides for mechanical stability on the one hand; on the other hand it has, due to the high void volume, a very low resistance of transport of molecules through the membrane when the voids are filled with water. The third layer has, in one embodiment of the present invention, a thickness of 20 to 60 μm.

The fourth layer is the outer layer, which is characterized by a homogeneous and open pore structure with a defined surface roughness. In one embodiment, the number average size of the pore openings is in the range of 0.5 to 3 μm, further the number of pores on the outer surface is in the range of 20,000 to 100,000 pores per mm$^2$. In one embodiment, this fourth layer has a thickness of about 1 to 10 μm.

Generally, the capillary dialyzer comprises from 2,500 to 14,000 hollow fiber membranes, for instance, from 8,000 to 13,000 fibers. The nominal surface area of the hollow fiber membranes in the capillary dialyzer usually is in the range of from 0.25 to 2.5 m$^2$, for instance, 1.2 to 2.1 m$^2$. The capillary dialyzer has an effective membrane surface area in the range of from 0.2 to 2.2 m$^2$, for instance, 1.1 to 2.1 m$^2$.

The capillary dialyzers of the invention can belong to any of the known dialyzer families: low-flux, high-flux, protein leaking, or high cut-off dialyzers. The membranes in the respective dialyzer families have the following structural characteristics (for a detailed discussion see Boschetti-de-Fierro et al: "Extended characterization of a new class of membranes for blood purification: The high cut-off membranes", Int. J. Artif. Organs 36 (2013); published online May 10, 2013):

| Dialyzer type | MWRO [kDa] | MWCO [kDa] | Pore radius [nm] |
|---|---|---|---|
| Low-flux | 2-4 | 10-20 | 2-3 |
| High-flux | 5-10 | 25-65 | 3.5-5.5 |

| Dialyzer type | MWRO [kDa] | MWCO [kDa] | Pore radius [nm] |
|---|---|---|---|
| Protein leaking | 2-4 | 60-70 | 5-6 |
| High cut-off | 15-20 | 170-320 | 8-12 |

MWRO: molecular weight retention onset
MWCO: molecular weight cut-off

EXAMPLES

Comparative Example 1

Using standard state-of-the-art processes, capillary dialyzers were produced from a bundle of 12,960 crimped hollow fiber membranes. Fiber crimp had a wavelength of 7.5 mm and an amplitude of 0.3 mm. The individual fibers had an outer diameter of 250 μm. The dialyzers had a cylindrical housing with an inner diameter of 38 mm. Packing density of the fibers within the dialyzers thus was 56.1%. Effective fiber length was 236 mm; effective membrane surface area was 1.73 m². The dialyzers were packed in sterile bags and steam-sterilized at 121° C.

Clearance of urea and vitamin B12 of six capillary dialyzers were measured according to EN1283. The dialyzers were operated in hemodialysis mode using a dialysis flow rate of $Q_D$=500 ml/min, a blood flow rate of $Q_D$=400 ml/min, and an ultrafiltration rate UF of 0 ml/min. The results obtained are summarized in the following table.

| Clearance [ml/min] | Mean | STD |
|---|---|---|
| Urea | 356 | 2 |
| Vitamin B12 | 245 | 2 |
| Cytochrome C | 170 | 0 |

Example 1

Using standard state-of-the-art processes, capillary dialyzers were produced from a bundle of 12,960 hollow fiber membranes. 11,520 fibers (89%) had a crimp with a wavelength of 7.5 mm and an amplitude of 0.3 mm. The bundle contained 1,440 non-crimped fibers (11%) evenly distributed throughout the bundle. The individual fibers had an outer diameter of 250 μm. The dialyzers had a cylindrical housing with an inner diameter of 38 mm. Packing density of the fibers within the dialyzers thus was 56.1%. Effective fiber length was 236 mm; effective membrane surface area was 1.73 m². The dialyzers were packed in sterile bags and steam-sterilized at 121° C.

Clearance of urea and vitamin B12 of six capillary dialyzers were measured according to EN1283. The dialyzers were operated in hemodialysis mode using a dialysis flow rate of $Q_D$=500 ml/min, a blood flow rate of $Q_D$=400 ml/min, and an ultrafiltration rate UF of 0 ml/min. The results obtained are summarized in the following table.

| Clearance [ml/min] | Mean | STD |
|---|---|---|
| Urea | 358 | 1 |
| Vitamin B12 | 252 | 2 |
| Cytochrome C | 184 | 1 |

The invention claimed is:

1. A capillary dialyzer comprising a housing and a bundle of semi-permeable hollow fiber membranes disposed therein, characterized in that the bundle of hollow fiber membranes comprises from 85 to 95% crimped fibers and from 5 to 15% non-crimped fibers, relative to the total number of fibers in the bundle.

2. The capillary dialyzer of claim 1, wherein the bundle of hollow fiber membranes comprises from 88 to 92% crimped fibers and from 8 to 12% non-crimped fibers.

3. The capillary dialyzer of claim 1, wherein the packing density of the hollow fiber membranes in the dialyzer is 55 to 65%.

4. The capillary dialyzer of claim 1, wherein the fibers have a sinusoidal texture with a wavelength in the range of from 6 to 9 mm.

5. The capillary dialyzer of claim 4, wherein the amplitude of the sinusoidal texture is in the range of from 0.1 to 0.5 mm.

6. The capillary dialyzer of claim 1, wherein the hollow fiber membranes have an outer diameter of from 150 to 320μm.

7. The capillary dialyzer of claim 1, wherein the fiber bundle in the dialyzer has a diameter of from 20 to 50 mm.

8. The capillary dialyzer of claim 1, wherein the effective fiber length within the bundle is in the range of from 120 to 280 mm.

9. The capillary dialyzer of claim 1, wherein the effective membrane surface area of the hollow fiber membranes within the dialyzer is in the range of from 0.25 to 2.5 m².

10. The capillary dialyzer of claim 9, wherein the effective membrane surface area of the hollow fiber membranes within the dialyzer is in the range of from 1.1 to 2.1 m².

11. The capillary dialyzer of claim 1, wherein the semi-permeable hollow fiber membranes comprise 80-99 wt % of polysulfone or polyethersulfone; and 1-20 wt % of polyvinylpyrrolidone.

12. The capillary dialyzer of claim 1, wherein the semi-permeable hollow fiber membranes comprise a polyamide.

13. The capillary dialyzer of claim 1, wherein the semi-permeable hollow fiber membranes comprise a copolymer of acrylonitrile and sodium methallylsulfonate.

14. The capillary dialyzer of claim 1, wherein the semi-permeable hollow fiber membranes comprise a polyacrylonitrile.

* * * * *